United States Patent
Wong et al.

(10) Patent No.: US 9,265,880 B1
(45) Date of Patent: Feb. 23, 2016

(54) ONE-TIME USE CARTRIDGE FOR A SYRINGE INJECTOR

(71) Applicant: Aurum Medicare Pte Ltd., Singapore (SG)

(72) Inventors: Martin Wong, Singapore (SG); Isao Ochi, Singapore (SG); Juan Antonio S. Salgado, Moerschwil (CH)

(73) Assignee: Aurum Medicare Pte Ltd, Singapore (SG)

( * ) Notice: Subject to any disclaimer, the term of this patent is extended or adjusted under 35 U.S.C. 154(b) by 0 days.

(21) Appl. No.: 14/604,517

(22) Filed: Jan. 23, 2015

(51) Int. Cl.
*A61M 5/145* (2006.01)

(52) U.S. Cl.
CPC ... *A61M 5/1452* (2013.01); *A61M 2005/14573* (2013.01)

(58) Field of Classification Search
CPC .......... A61M 5/14546; A61M 5/1452; A61M 2005/14573
USPC ......... 604/151–155, 218, 221, 222, 239, 131, 604/201; 600/431–435; 128/DIG. 12, 13
See application file for complete search history.

(56) References Cited

U.S. PATENT DOCUMENTS

| | | | |
|---|---|---|---|
| 5,383,858 A * | 1/1995 | Reilly | A61M 5/14546 604/131 |
| 6,080,136 A * | 6/2000 | Trull | A61M 5/14546 128/DIG. 1 |
| 6,336,913 B1 | 1/2002 | Spohn et al. | |
| 6,533,758 B1 | 3/2003 | Staats et al. | |
| 6,764,466 B1 * | 7/2004 | Staats | A61M 5/14546 604/154 |
| 8,147,463 B2 | 4/2012 | Hieb et al. | |
| 8,366,679 B2 | 2/2013 | Cole et al. | |
| 8,572,834 B2 | 11/2013 | Cude | |
| 8,597,246 B1 * | 12/2013 | Fago | A61M 5/14546 604/131 |

* cited by examiner

*Primary Examiner* — Manuel Mendez
(74) *Attorney, Agent, or Firm* — Thomas Schneck (57) ABSTRACT

A one-time use cartridge for a CT or MRI syringe has a syringe body coupled to an adapter by flanges that are trapped by a locking tooth supported as part of a groove in a unitary adapter. One-time use is enhanced with one-way valves associated with the forward end of the syringe body. The one-way valves have coaxial inner and outer members with reversed roles for fluid inflow and outflow tubing connections. The valves operate under positive and negative pressure generated by the syringe piston.

14 Claims, 8 Drawing Sheets

ONE-TIME USE CARTRIDGE FOR A SYRINGE INJECTOR

TECHNICAL FIELD

The invention relates to syringe adaptor plunger systems used with automated syringes for CT/MRI injection systems.

BACKGROUND ART

Due to increasing awareness of physician concerns regarding patient safety, the use of disposable syringe-based medical injector systems has become standard hospital practice. The problem for patients, physicians, and the healthcare system in general is that typically proprietary syringe and medical injector systems are costly. A significant cost arises because in the consumable portion of the system only matched proprietary syringes and plungers will work with the proprietary system. Adaptors for the consumables which can provide an interface with fixed system components could provide a more cost effective solution while still providing safety to the patient. Additionally, there is the significant health risk of air being entrapped in the syringe body during connection to the system. A syringe which can safely release air entrapped during connection to the adaptor components will provide increased safety while continuing to provide better options for the patient.

Currently, many hospitals use CT injection systems such as Medrad's Stellant System or PolyTen Plastics syringe adapter systems. Various systems of the prior art are releasable, disposable, front-loading medical syringe systems for the controlled medical electro-mechanical injection.

U.S. Pat. No. 6,080,136 to Trull et al. shows a front-load syringe injector system that includes a front-load injector having mounted on a front face a detachably engageable adapter. A driving head is engaged with a drive mechanism of the injector and the driving head disengageably engages a plunger mounted in a syringe mounted on the adapter. At least one of the plunger and driving head and syringe elements interacts with the adapter to effect engagement and disengagement of the plunger and driving head and syringe with respect to one another. Flanges on the injector fit into the adapter.

U.S. Pat. No. 5,383,858 to D. Reilly et al. discloses a front-loading syringe having a movable plunger for injecting liquid that is rotatably mountable on a front wall of an injector housing. The plunger has an interference fit in sealed relationship with respect to the syringe by a first quick release mechanism. At the same time, the plunger is connected to an injector drive mechanism by a second releasable mechanism. An injection end of the syringe comprises an injector portion of reduced diameter inside a screw-threaded attachment portion of larger diameter, and may include loop-shaped reinforcing handle portions.

U.S. Pat. No. 6,764,466 to P. Staats et al. discloses a syringe adapter that includes a channel for receiving a rearward end of a syringe. First and second mounting flanges on the adapter overlay a portion of the channel, to cooperate with mounting flanges on a rearward end of the syringe, so that the syringe mounting flanges may be inserted between the adapter mounting flanges, and then rotated in the channel behind the adapter mounting flanges, to thereby lock the syringe to the adapter. The adapter further includes one or more locking pins, which in a locked position extend across the channel, to block the syringe from rotating in the channel and thereby prevent a syringe from being dismounted from the adapter. A collar incorporated in the adapter interacts with a drive ram of the injector to move the locking pins into their locked position whenever the ram is forward of a rearwardmost position. A ram tip adapter includes a movable member having a connector for engaging a rearward face of a plunger.

U.S. Pat. No. 8,597,246 to Fago et al. discloses a front-loading injector, for preventing leakage of spilled fluid from an external surface of a syringe into the vicinity of the drive ram. A sealing gasket may be incorporated into the front face of the injector housing, for mating to the rearward circular edge of the cylindrical body of a syringe. Alternatively, sealing and locking functions may be performed by a single structure on the rearward end of the syringe. Leakage may be prevented by including a non-planar sealing flange on the syringe, positioned on the syringe forward of the locking structure, or by a two-piece structure, including a syringe and a separate leakage stopping washer for surrounding the syringe to halt the flow of, fluid along the exterior of the syringe. The syringe may include an annularly discontinuous flange forward of the locking structure, for providing mechanical support for the syringe against the injector.

An object of the invention is a simpler, lower cost, yet safe syringe adapter and plunger adapter combination for CT/MRI syringes.

SUMMARY

The above object has been met with a one-time use cartridge for a CT or MRI syringe fitting between a syringe piston housing and a needle. The cartridge consists of two main members and a piston extender member. The two main members are a unitary tubular adapter and a syringe body coaxial with the tubular adapter.

A first end of the tubular adapter is gripped in a coaxial piston housing. The second end of the tubular adapter has a segmented receiving groove bayonet mount with an upper side of the groove mount having alternating groove segments being relief and overhang segments. The overhang segments have a cantilevered axially extending tooth supported near an overhang segment end. A front loading syringe body is coaxially joinable to the tubular adapter. The syringe body has a segmented flange base with the flange base segments snugly fitting into relief segments of the upper side of the groove mount of the tubular adapter.

The overhang segments of the groove mount have a circumferential length greater than a base flange segment so that rotation of a base flange segment in the groove mount forces axial direction raising of the cantilevered tooth, bending the groove mount, until rotation of the base flange segment passes the tooth. The cantilevered tooth is released from the tension induced by bending, moving to block counter rotation of the base segment and snapping down onto the base flange segment, holding the flange segment securely in place, creating a fluid seal.

The permanently joined unitary tubular adapter and syringe body form a disposable cartridge for use with an automated CT or MRI machine. One-way coaxial valves are mounted on a nose portion of the syringe body. One such one-way valve is axially mounted for fluid outflow. At least one other one-way valve is non-axially mounted for fluid inflow.

Inner and outer coaxial members are fittings, for example, for tubing. The roles of the inner and outer fittings are reversed for fluid inflow and fluid outflow so that an inflow reservoir cannot be connected to an outflow member. The one way valve fittings may be leur fittings but arranged as one-way valve members, for example by one-way bayonet joinder.

Piston motion supplies vacuum pressure for drawing fluid into the syringe body or positive body pressure to expel fluid through the one-way valve at the nose of the syringe body.

DESCRIPTION OF INVENTION

Figure 1:
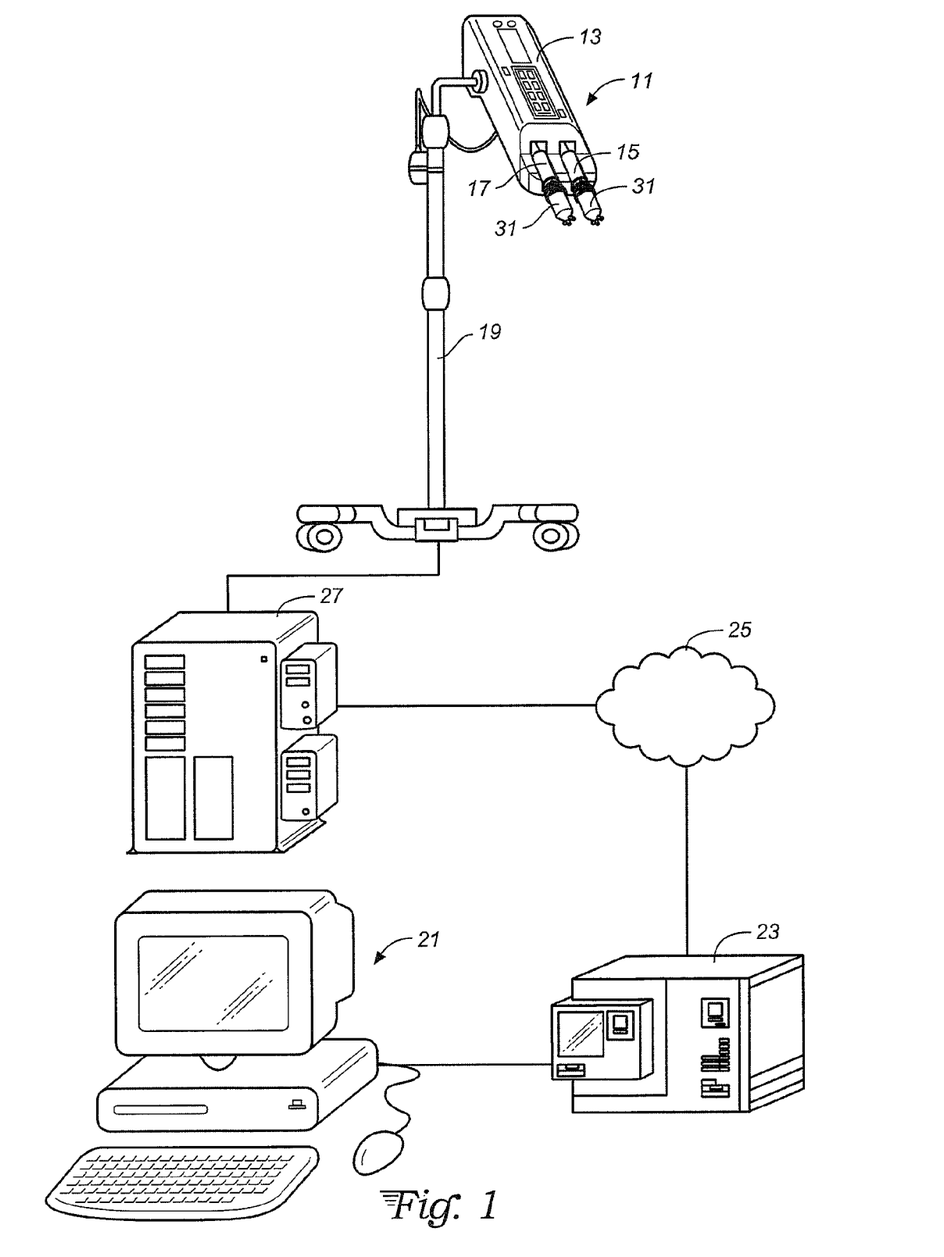
FIG. 1 is a plan view of an automated CT or MRI syringe system supporting the one-time use cartridge of the present invention.

With reference to FIG. 1, an automated CT or MRI syringe system of the prior art, such as the Medrad Stellant Injection System, a trademark of Bayer Healthcare, is shown having a syringe holder 13 supporting syringes 15 and 17 from a floor mounted pole 19 in a medical facility. The syringe holder 13 contains electronics that drive a piston in each of the syringes 15 and 17. A workstation 21, operated by a clinician, communicates with a local server 23 that may be connected to a number of similar workstations. The server stores data to and from the injection system and communicates to a controller 27 for the injection system through a network 25. The present invention is a disposable cartridge 31 associated with each of the syringes 15 and 17.

Figure 2:
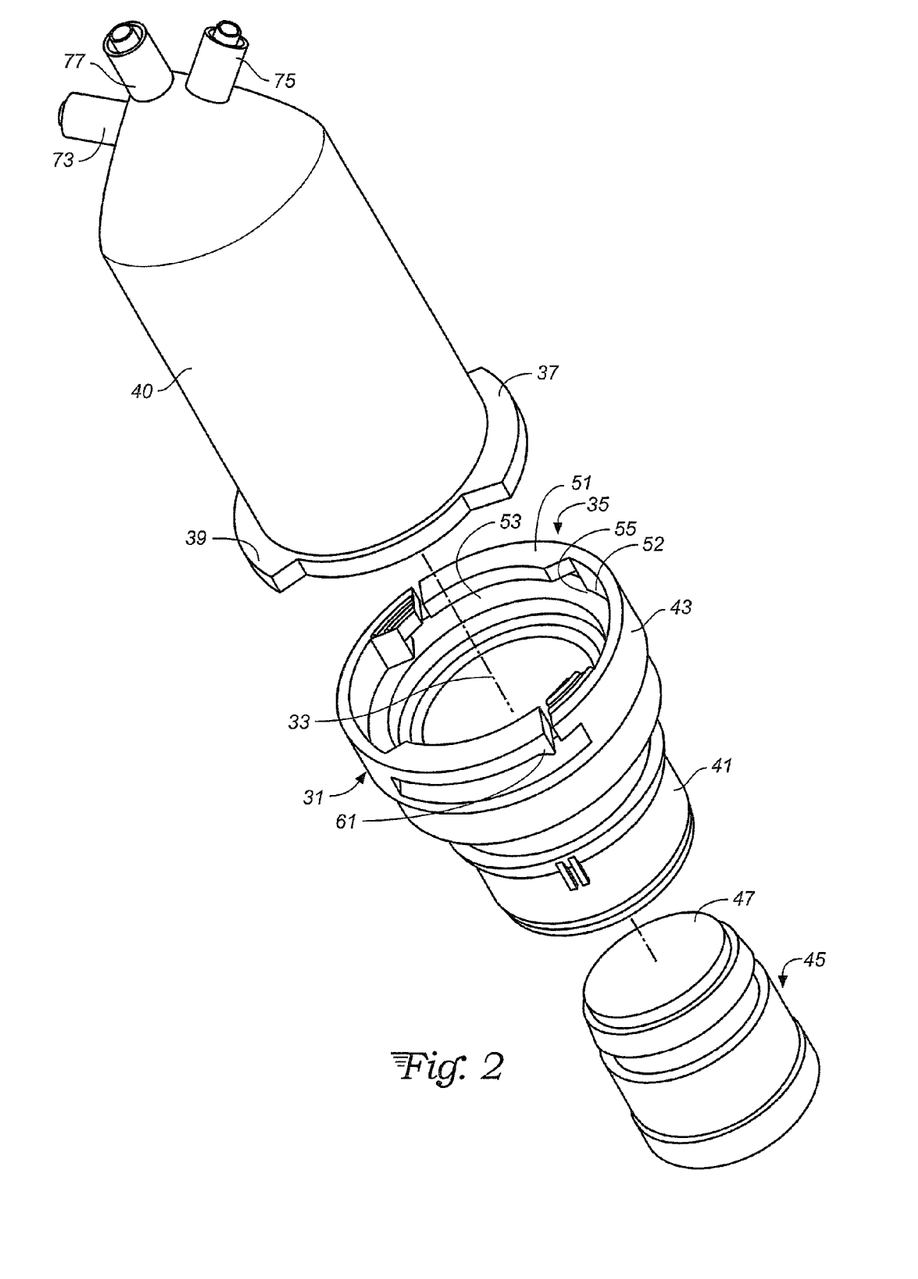
FIG. 2 is an exploded perspective view of a one-time use cartridge shown in FIG. 1.

With reference to FIG. 2, a unitary tubular adapter 31 has an annular cross-sectional shape with an axis 33 with a bayonet mount 35 for receiving flanges 37 and 39 of the syringe body 40. The tubular adapter has a first end 41 with a first outside diameter and a second end 43 with a second outside diameter that is greater than the first outside diameter. The greater second outside diameter allows the second end 43 to have an inside diameter that matches the inside diameter of coaxial syringe body 41 so that fluid can flow through the joined tubular adapter and syringe body without restriction. The tubular adapter has an end to end volume that may be comparable to the volume of the syringe body and in some instances exceed the volume of the syringe body. Sometimes the first fluid volume of the adapter exceeds the second fluid volume of the syringe body but usually the first and second volumes are within a volumetric range of 50% of each other. The combined volume can be as low as 50 ml, or lower, but a typical combined volume typically exceeds 125 ml and sometimes exceeds 160 ml, depending on the fluids being used, the needs of the patient and medical equipment considerations. Fluid volumes are selectable for both the tubular adapter and the syringe body until the two members are joined. After joinder, the combined volume may not be varied.

The tubular adapter is typically made of polymeric material, molded in a single piece. The tubular adapter extends the syringe length so that the syringe piston must be extended in order to push fluid through the length of the syringe body 40. A hollow piston extender 45 of annular cross section is coaxial with tubular adapter 31. A flat upper surface 47 provides a cup shape so that the piston extender may form a rigid cap for a piston of a syringe system, being adhered or frictionally engaged in place and slideable within the unitary tubular adapter and the syringe body until the upper surface 47 of the piston extender can no longer advance in the syringe body 40. One-way valves 73 and 75 into the syringe body and one-way valve 77 out of the syringe body are explained below.

The bayonet mount 35 of the tubular adapter 31 has a segmented receiving groove that is defined by an upper side with alternating overhang 51 and relief 52 segments and a spaced apart lower side 53. In other words, portions of upper side are cut away or relieved, while overhang segments 51 are not cut away or relieved, allowing flanges 37 and 39 to enter the groove between overhang segments that are longer than the flanges. An overhang segment has a downwardly extending tooth 61 that will serve to lock a corresponding flange in place when a flange rotates in a groove beneath a tooth, then past a tooth forcing the tooth to snap down on the flange, locking it in place.

Figure 3:
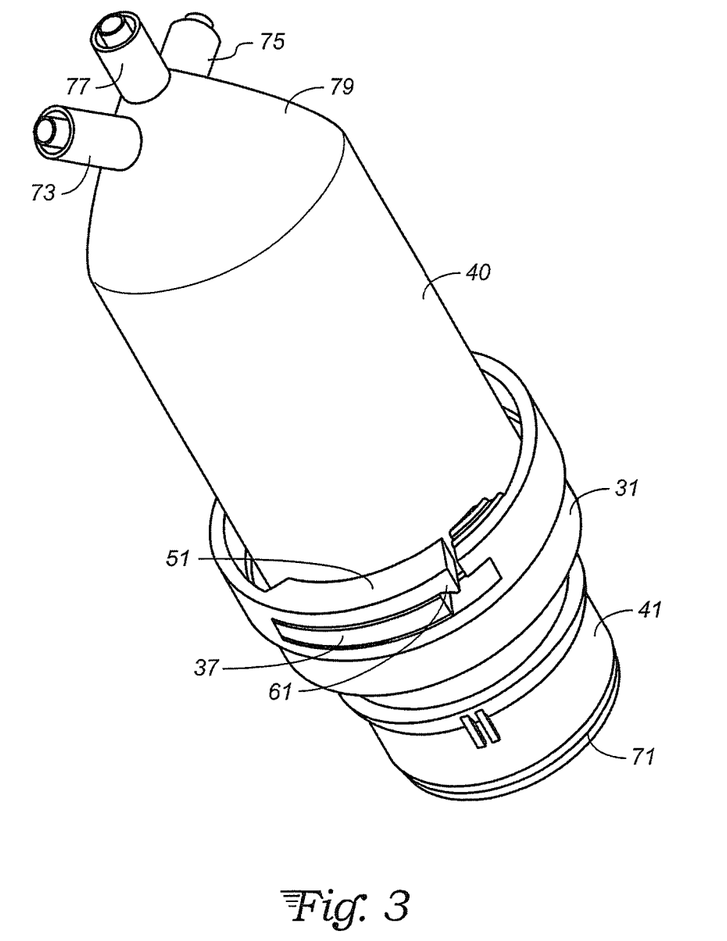
FIG. 3 is a perspective view of the cartridge of FIG. 2 in a joined member disposable configuration.

With reference to FIG. 3, the unitary tubular adapter 31 is seen to lock to syringe body 40, having entered the groove in the unitary tubular adapter and then experienced clockwise rotation. Flange 37 is a radially outwardly extending part of syringe body 40 that is locked in the groove formed by upper and lower sides described above, trapped by the downwardly extending tooth 61, preventing counterclockwise rotation. The first end 41 of the tubular adapter has annular ribs 71 for gripping by a syringe holder, part of the electronic apparatus seen in FIG. 1. The electronic apparatus may have sensors for gauging the insertion extent of the tubular adapter, either with electromechanical or optical sensors. In the joined configuration of FIG. 3, the unitary tubular adapter 31 and the syringe body form a cartridge for an automated CT or MRI syringe system, ready to receive medication fluid through one or both of the one-way valves 73 and 75, filling the volumes of the tubular adapter 31 and the syringe body 40 as permitted by the upper surface of the piston extender. The piston extender is then advanced expelling air through the one-way outflow valve 77 until fluid starts to be emitted from the outflow valve. A hypodermic needle can be added to the outflow valve before expelling air to clear the needle of air as well as the cartridge. A conical nose 79 of the syringe body 40 stops the advance of the piston extender. The exterior of the outflow and inflow valves have ever lock fittings for attachment of external hoses or additional valves or a needle.

Figure 4:
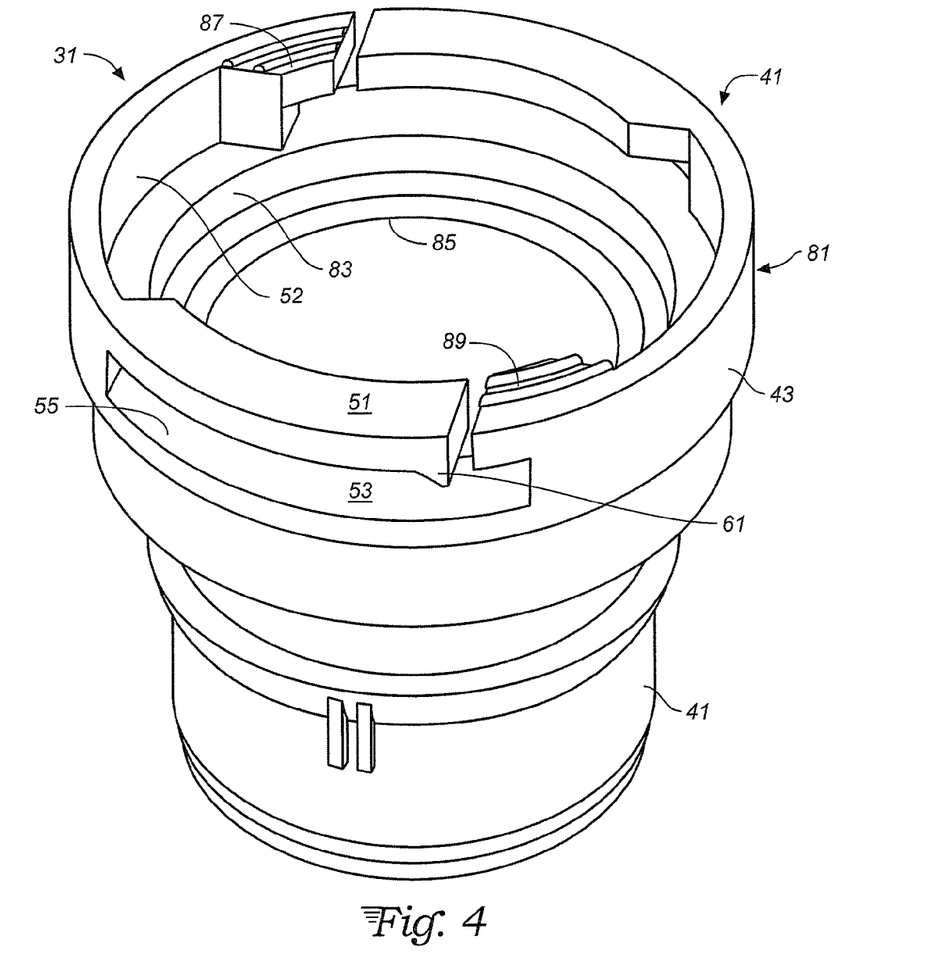
FIG. 4 is a front perspective view of a unitary tubular adapter shown in FIG. 2.

With reference to FIG. 4, the unitary tubular adapter 31 is seen to have a second end 43 with a second outer diameter 81 and a second stepped inner diameter 83. The reason that the second inner diameter is stepped is that there is a first inner diameter 85 associated with the first end of the tubular body that matches the inner diameter of the syringe body. The step allows the groove of the tubular adapter to receive the flanges of the syringe body without impairment of the passageway through tubular adapter compared to the passageway through the syringe body. This is because the inner rim of the syringe body rests on the lowermost adapter step allowing the inside diameter of the syringe body to match the first inner diameter 85 of the tubular adapter body for a smooth tunnel through both the tubular adapter and the syringe body. Outer diameter 81 is also stepped so that the presence and size of a cartridge may be senses by a machine from sizes of steps or outer diameters. Volumetric sizes of cartridges may be indicated to a machine by sizes of steps in the outer diameter 81. Note that the tubular adapter is a single piece of material. The groove 55 has an upper side associate with overhang segment 51 and lower side 53. A relief segment 52 is adjacent to the overhang segment and has a length sufficient to allow entry of a syringe body flange. Upon clockwise rotation of the flanges, a flange will enter beneath the overhang segment 51, bending it upwards as the cantilevered tooth 61 cams upwardly until the flange passes the tooth 61. When this happens the tooth 61 snaps downwardly bringing the overhang segment downward on top of the flange, locking the flange in place. Tail pieces 87 and 89 reside in the groove with portions adjacent the overhang segment, adjacent to the tooth, blocking fluid leakage trough the groove when flanges are fully seated. There is only a very small gap between the tail piece portions adjacent the overhang segment to allow the tooth to move, but close adjacency is needed to block fluid leakage.

Figure 5:
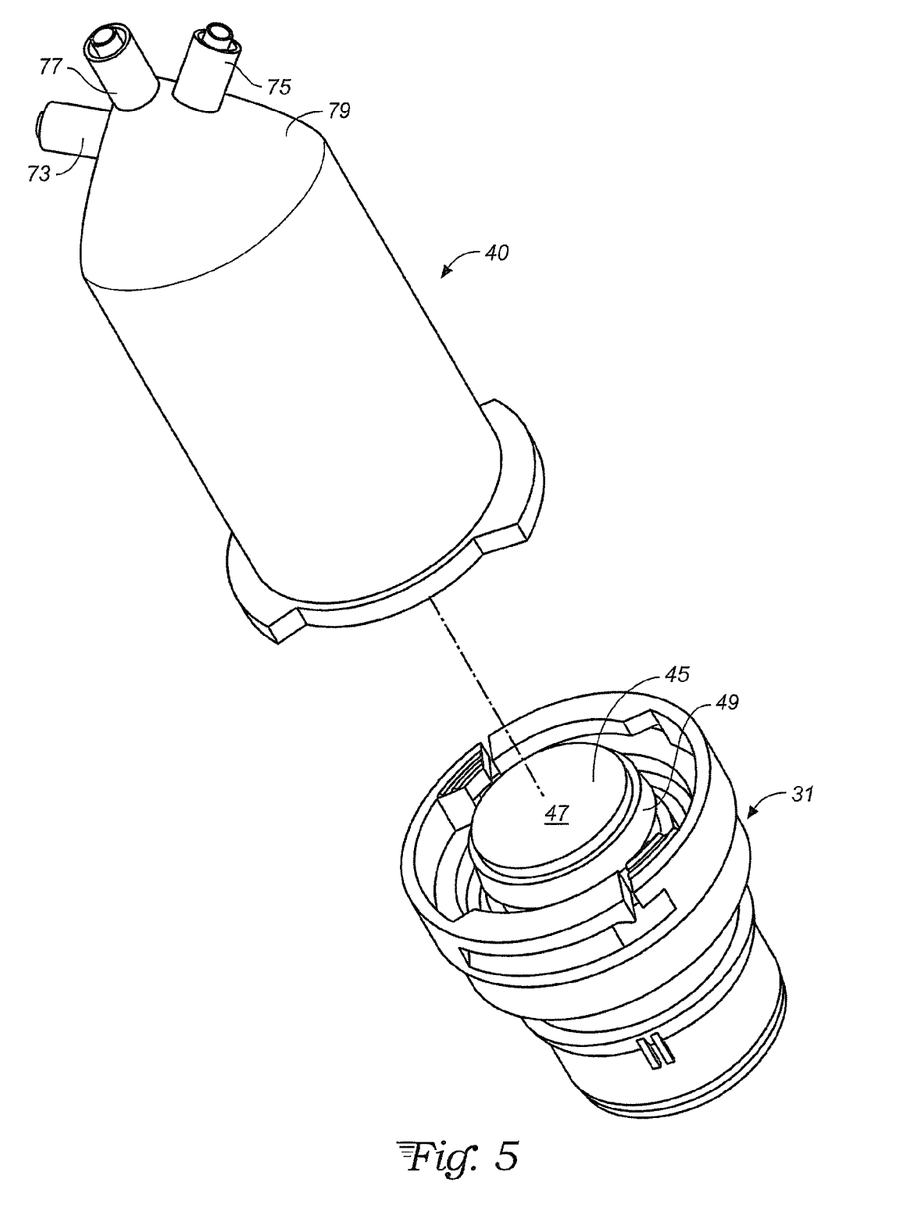
FIG. 5 is an exploded perspective view of the cartridge of FIG. 2 with a piston extender member within the tubular adapter.

With reference to FIG. 5, the piston extender 45 is seen to be coaxial along axis 33 with the tubular adapter 31 and the syringe body 40. Below the upper piston surface 47 is an annular exterior portion 49 that is sloped to form an annular ridge for contact with the interior of conical nose 79 of the syringe body thereby stopping motion of the piston.

Filling of the syringe body with contrast media in the prior art frequently involved use of a leur at the end of the syringe and pulling the piston back to suck contrast media out of a vial. Contamination can occur by touching parts over which the media flows. Sometimes the syringe body is filled through a spike tip at the end of the syringe with a vial attached to the spike that is penetrated by the spike. This procedure is limited to small vials and contamination in touching the spike or the penetrated part of the vial. There is also risk of re-use of the spike with another vial.

Figure 5A:
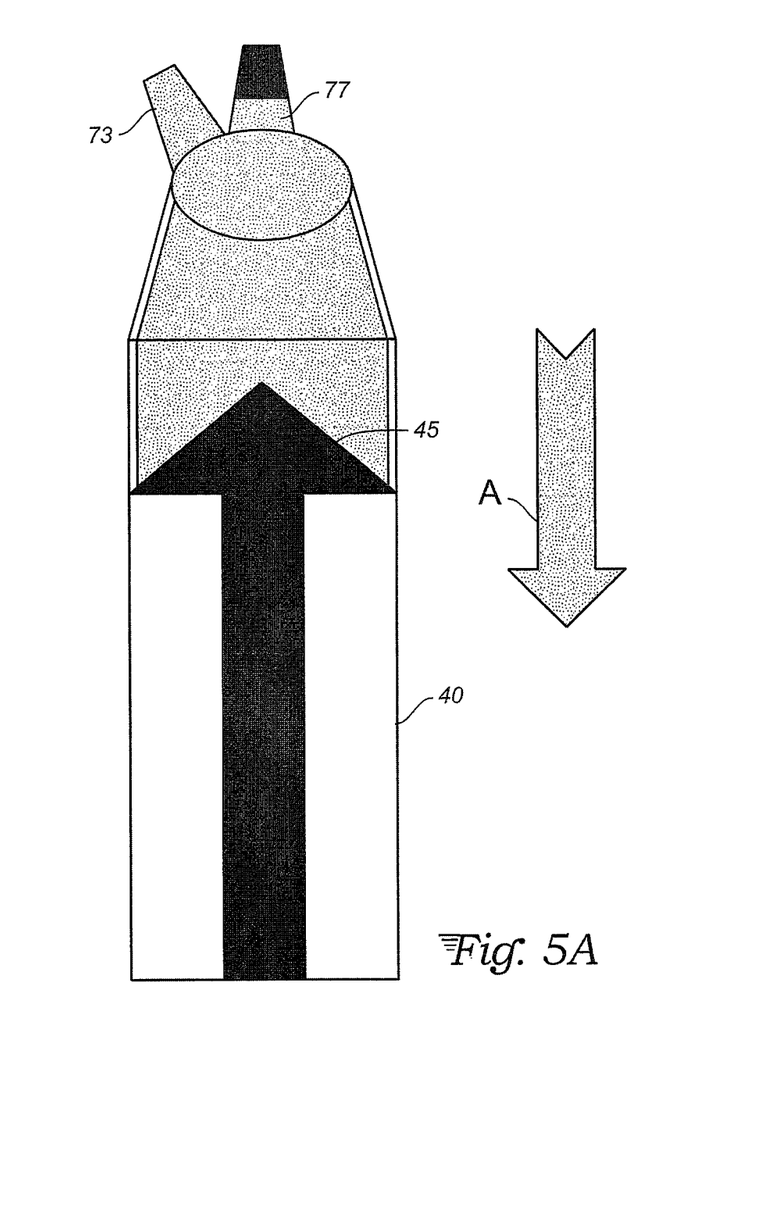
FIGS. 5A and 5B are operation plan views of the cartridge of FIG. 2.
Figure 5B:
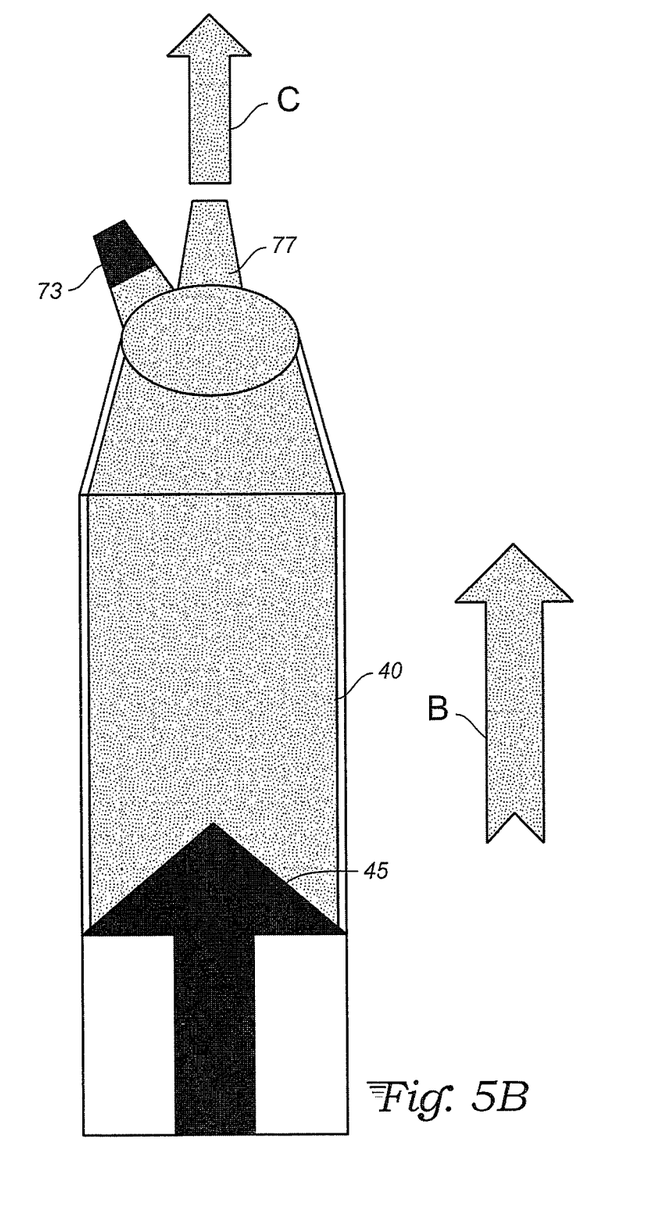

The present invention takes two approaches to eliminate contamination. First there is a separation of inflow and outflow liquids. Secondly a one-way valve 77 into the syringe body 40 on piston downstroke, shown in FIG. 5A, is closed while one-way valve 73 is open allowing liquid into the syringe body under vacuum pressure as piston extender 45 moves down in the direction of arrow A. When piston pressure is reversed, as shown in FIG. 5B, one-way valve 77 is open, while one-way valve 73 leading to a liquid supply is closed as piston extender 45 moves up in the direction of arrow B and fluid flows towards a patient in the direction of arrow C.

The one-way valves 73, 75, and 77 shown in FIG. 5 are shown as having coaxial fittings with inner and outer members joined together. Valve 77 may have the outer valve member associated with tubing going to the patient, while the inner member is fixed to the syringe body 40. Valves 73 and 75 are the opposite. The outer valve members are fixed to the syringe body, while the inner members are associated with tubing from supply vials. All valve members have similar dimensions. Accordingly tubing for inflow and outflow have different dimensions that cannot connect to the wrong valve. Coaxial one-way fittings may be bayonet locking type fittings.

Figure 6:
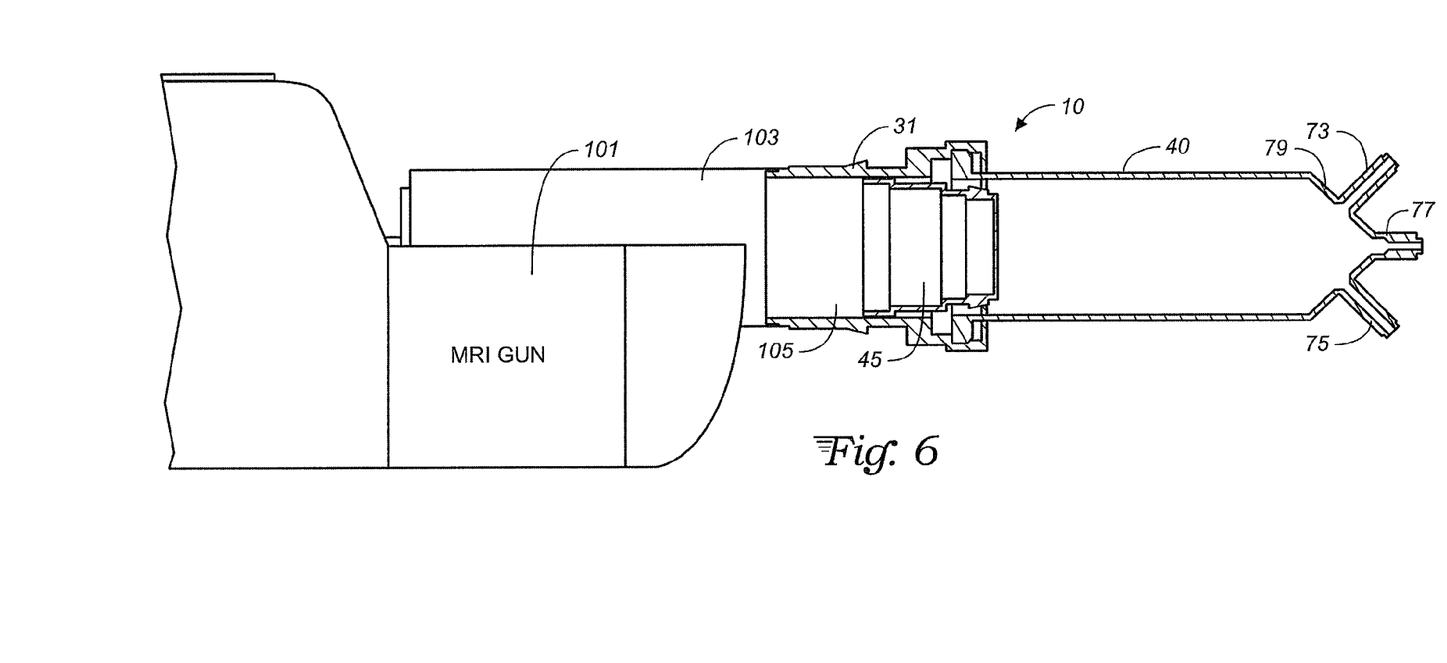
FIG. 6 is a side plan view of the cartridge of FIG. 2 as part of an automated CT or MRI syringe as shown in FIG. 1.

In operation, a CT or MRI machine actuator 101 has a piston driving unit 103 that grasps the tubular adapter 31 of cartridge 10. The machine piston 105 drives the attached piston extender 45 into the syringe body 40 to a commanded extent, or until the piston extender contacts conical nose 79. As the piston moves forward, fluid is expelled through the one way valve 77. When the piston moves in the reverse direction, fluid may be drawn into the syringe body through one way valves 73 and 75. Once the piston is advanced to expel fluid, the piston may not be withdrawn or reset until cartridge 10 is removed and a new cartridge installed. After cartridge 10 is removed, it may not be disassembled for reuse, but must be discarded since the machine may require that the piston be reset with a tubular adapter in place. Once the piston is reset, the syringe body may be locked onto the tubular adapter. The piston cannot be reset with the syringe body in place.

The unitary construction of the tubular adapter provides for low cost manufacturing and simplicity in use, while simultaneously providing for patient safety by one-time restricted use in the cartridge.

What is claimed is:

1. A cartridge for one-time use in an automated electronic syringe fitting between a syringe piston housing and a needle comprising:

a unitary tubular adapter holding a first fluid volume and having a first end of a first inside and a first outside diameter to be gripped in a co-axial piston housing and a second end of a second outside diameter greater than the first outside diameter and having a segmented receiving groove bayonet mount with an upper side of the groove mount having alternating groove segments being relief and overhang segments, with the overhang segments having a cantilevered axially extending tooth supported near an overhang segment end; and a syringe body holding a second fluid volume and co-axially joinable to the tubular adapter having an inside diameter matching the first inside diameter of the tubular adapter at a region near the co-axial joinder with the tubular adapter and having a segmented flanged base, whereby the first and second fluid volumes are in fluid communication, the base flange segments snugly fitting into the relief segments of the upper side of the groove mount of the tubular adapter, the overhang segments of the groove mount having a circumferential length greater than a base flange segment whereby rotation of a base flange segment in the groove mount forces axial direction raising of the cantilevered tooth under cantilever tension until rotation of the base flange segment passes the tooth wherein the cantilevered tooth is released from tension moving to block counter-rotation of the base segment and snapping down onto the base flange segment creating a fluid seal and an axial fluid path along the matched inside diameters of the tubular adapter and syringe body, the syringe body having a conical nose terminating in an axial one-way valve for fluid outflow from the syringe body and a non-axial one-way valve for fluid inflow from a fluid supply into the syringe body, the syringe body suitable for one-time use with the tubular adapter.

2. The apparatus of claim 1 further comprising an axially symmetric piston extender having an upper piston surface and an annular portion forming a sliding seal with the matching inside diameter of the tubular adapter and the syringe body, the piston extender positioned to push fluid from the first fluid volume to the second fluid volume.

3. The apparatus of claim 2 wherein the syringe body has a conical nose with a radially convergent second inside diameter distal to the tubular adapter and the piston extender has an annular ridge for wedging against the convergent second inside diameter wherein the piston extender cannot be retracted from the syringe body after fluid is pushed from the first fluid volume to the second fluid volume.

4. The apparatus of claim 2 wherein said piston extender has a hollow interior below the upper piston surface with axially spaced circumferential ridges of diminishing radii in said hollow interior for friction gripping of diverse piston diameters.

5. The apparatus of claim 1 wherein the one-way valve are coaxial valves having one of inner and outer valve members attached to the syringe body, wherein one of the inner and outer valve members for fluid inflow is different in being an inner or outer member from the inner and outer member for fluid outflow.

6. The apparatus of claim 5 wherein said conical nose has a first non-axial valve for fluid inflow.

7. The apparatus of claim 6 wherein said conical nose has a second non-axial valve for fluid inflow.

8. The apparatus of claim 1 wherein the first end of the tubular adapter has axial spaced circumferential ridges of diminishing radii on the first outside diameter thereof for friction gripping of the piston housing.

9. The apparatus of claim 8 wherein the first end of the tubular adapter has an outwardly flared ridge on the first outside diameter thereof to stop gripping by the piston housing.

10. The apparatus of claim 8 wherein the tubular adapter, dispense head and piston extender are in sealed fluid relation relative to the piston housing.

11. The apparatus of claim 1 wherein the first fluid volume of the adapter exceeds the second fluid volume of the syringe body.

12. The apparatus of claim 1 wherein the first and second volumes are within a volumetric range of 50% of each other and exceeding a combined volume of 50 ml.

13. The apparatus of claim 12 wherein the first and second combined volumes exceed 125 ml.

14. The apparatus of claim 12 wherein the first and second combined volumes exceed 160 ml.

* * * * *